US005800472A

United States Patent [19]
Mann

[11] Patent Number: 5,800,472
[45] Date of Patent: Sep. 1, 1998

[54] RECOMMENDED REPLACEMENT TIME TRIGGER FOR USE WITHIN AN IMPLANTABLE RATE-RESPONSIVE PACEMAKER

[75] Inventor: Brian M. Mann, Edgartown, Mass.

[73] Assignee: Pacesetter, Inc., Sylmar, Calif.

[21] Appl. No.: 802,624

[22] Filed: Feb. 19, 1997

Related U.S. Application Data

[60] Provisional application No. 60/016643 May 14, 1996.
[51] Int. Cl.⁶ .................................................. A61N 1/378
[52] U.S. Cl. .................................................. 607/29
[58] Field of Search ........................ 607/16, 29, 27, 607/34

[56] References Cited

U.S. PATENT DOCUMENTS

| | | |
|---|---|---|
| 4,448,197 | 5/1984 | Nappholz et al. ............ 607/29 |
| 5,031,616 | 7/1991 | Mann et al. .................. 607/29 |
| 5,193,538 | 3/1993 | Ekwall ........................ 607/29 |
| 5,228,439 | 7/1993 | Mann et al. .................. 607/29 |
| 5,620,474 | 4/1997 | Koopman ..................... 607/29 |

Primary Examiner—William E. Kamm
Assistant Examiner—Kennedy J. Schaetzle

[57] ABSTRACT

A multi-mode rate-responsive pacemaker provides an accurate recommended replacement time (RRT) indicator which provides for full rate response performance until RRT is indicated without any decrease in longevity due to a premature triggering of RRT during rate response. An RRT trigger signal is generated whenever the battery voltage falls below a prescribed RRT threshold voltage. In one embodiment, a sustained battery voltage (determined based, e.g., on a long-term average of the battery voltage) that is less than the RRT threshold voltage must be detected before the RRT trigger signal is generated. In another embodiment, two RRT threshold voltages are used rather than one. A normal RRT threshold voltage is used when the pacer is not operating in a rate-responsive mode, and a lower RRT threshold voltage is used when the pacer is operating in a rate-responsive mode. In yet another embodiment, when the pacemaker is operating in a rate-responsive mode, the RRT trigger signal is not generated until a time delay longer than a typical exercise duration has elapsed during which the battery voltage continuously remains below the RRT threshold.

18 Claims, 8 Drawing Sheets

RECOMMENDED REPLACEMENT TIME TRIGGER FOR USE WITHIN AN IMPLANTABLE RATE-RESPONSIVE PACEMAKER

This application claims the benefit of U.S. Provisional Application 60/016,643, filed May 14, 1996.

FIELD OF THE INVENTION

The present invention relates to implantable medical devices and methods, and more particularly to an implantable rate-responsive pacemaker having an improved recommended replacement time (RRT) trigger.

BACKGROUND OF THE INVENTION

A well-known characteristic of an implantable pacemaker is that the internal impedance of the battery used within the pacemaker increases as the battery gets older and more depleted, thereby causing the output voltage of the battery to decrease for a given load or current. This characteristic is in fact used to help predict when it is time to replace the pacemaker so that new pacemaker having a new battery may be implanted. That is, during pacemaker operation, when a nominal current drain exists on the battery, the battery voltage is monitored. If the battery is getting old and/or if its cell energy is depleted, the resulting high internal impedance will cause the output voltage of the battery to drop. As soon as the battery voltage drops below a preset threshold, a recommended replacement time (RRT) trigger, or equivalent flag or signal, is set.

A common response within an implantable pacemaker to an RRT trigger is to cause an abrupt change, e.g., a 10% decrease, in the pacemaker's base pacing rate. Such sudden decrease in the base pacing rate not only serves to reduce the battery current drain (and therefore lengthen the remaining life of the battery), but also provides a detectable change in the pacemaker's performance that alerts the physician and/or patient of the need to plan for replacing the pacemaker soon.

Rate-responsive pacemakers are pacemakers that adjust the basic pacing rate as a function of a sensed parameter, e.g., body motion, the oxygen content of the patient's blood, etc., which parameter provides some physiological indication that there is a need to increase the patient's heart rate (as occurs naturally in a healthy person, e.g., when the person exercises). The heart rate indicated by the sensed parameter is typically referred to as the "sensor rate", or "sensor-indicated rate" (SIR). (Note: such parameter is typically sensed using a special sensor.) It is thus the function of a rate-responsive pacemaker to pace the heart, if needed, at a rate corresponding to the SIR. Rate-responsive pacemakers have become, during recent years, the pacemaker of choice for many patients who lead active life styles, or otherwise have a need for a pacemaker which automatically adjusts its basic pacing rate. Representative rate-responsive pacemakers are described, e.g., in U.S. Pat. Nos. 4,712,555; 4,940,052 and 4,788,980.

Disadvantageously, rate-responsive pacemakers suffer from the problem that the battery current drain increases, and therefore the battery voltage drops, during rate response, e.g., as the basic pacing rate increases (as would occur, e.g., when the patient is exercising). As a practical matter, this means that the RRT trigger may be tripped prematurely, i.e., RRT may be triggered when there is really no need to trigger the RRT. When RRT is triggered, however, not only does the basic pacing rate suddenly decrease, but the rate-responsive mode may be terminated, all of which could be deleterious to the patient. Thus, there is a need in the rate-responsive pacemaker art to make sure that RRT is not improperly triggered.

One prior art technique for handling RRT in a rate-responsive pacer involves gradually reducing the maximum sensor rate as RRT is approached. Disadvantageously, this method does not allow the pacemaker to achieve the maximum sensor rate prior to RRT, and/or reduces the longevity of the pacer by using the decrease in maximum sensor rate as an RRT criteria.

Another prior art technique for handling RRT in a rate-responsive pacer is to cause the RRT trigger to be activated and latched whenever the sensor-indicated rate is at its maximum value. Unfortunately, this method, upon triggering RRT, results in an abrupt decrease in rate, an abrupt loss of rate-response, and optionally a change in pacing mode.

It is thus evident that improvements in the RRT trigger of a rate-responsive pacemaker are needed.

SUMMARY OF THE INVENTION

The present invention addresses the above and other needs, in accordance with one aspect of the invention, by providing two RRT threshold voltages rather than one. Specifically, a normal RRT trigger threshold voltage is used when the pacer is not operating in a rate-responsive mode, and a lower RRT trigger threshold voltage is used when the pacer is operating in a rate-responsive mode. These two RRT triggers may be implemented as a simple RRT logical switch. When the pacer is operating in a non-rate-responsive mode, the RRT switch engages a normal RRT threshold voltage, $V0_{RRT}$. That is, RRT is not triggered unless the battery voltage drops below $V0_{RRT}$. When the pacer is operating in a rate-responsive mode, on the other hand, the RRT switch engages a reduced RRT threshold voltage, $V1_{RRT}$, where $V1_{RRT}$ is less than $V0_{RRT}$ by a prescribed amount, e.g., 200 mV. Thus, when the pacer is operating in a rate-responsive mode, RRT is triggered only when the battery voltage drops below $V1_{RRT}$.

In accordance with another aspect of the invention, a sustained battery voltage (determined, e.g., based on a long-term average of the battery voltage) must be detected that is less than the RRT threshold voltage before the RRT trigger signal is generated.

In accordance with yet another aspect of the invention, the RRT trigger comprises a time delay trigger having a time delay longer than a typical exercise duration. In operation, when the pacer is operating in a rate-responsive mode, the RRT trigger is not generated unless the battery voltage is less than a normal RRT threshold voltage, $V0_{RRT}$, and remains less than $V0_{RRT}$ for a continuous (or consecutively sampled) time-delay period T1. The time delay T1 is selected to be longer than the typical exercise duration, e.g., 4 hours.

It is a feature of the invention to provide for an accurate RRT indicator which provides for full rate response operation (e.g., without any reduction in maximum SIR) until RRT is indicated without any decrease in longevity due to a premature tripping of RRT during rate response.

BRIEF DESCRIPTION OF THE DRAWINGS

The above and other aspects, features and advantages of the present invention will be more apparent from the following more particular description thereof, presented in conjunction with the following drawings, wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
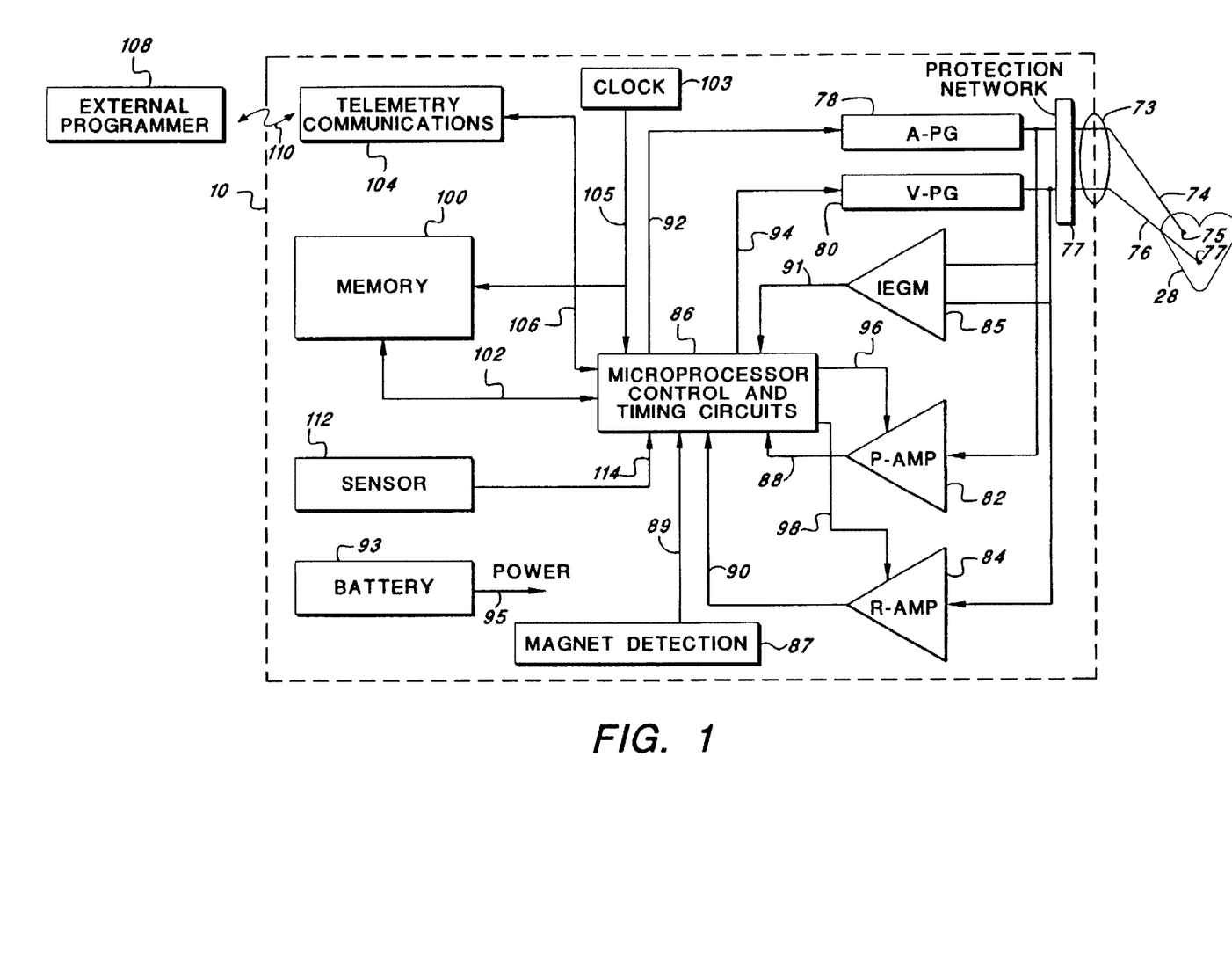
FIG. 1 shows a functional block diagram of an implantable, programmable, dual-chamber pacemaker, of a type with which the present invention may be used.

Turning first to FIG. 1, there is shown a functional block diagram of a dual-chamber pacemaker 10 of a type with which the present invention may be used. A brief explanation of the pacemaker 10 will first be presented in order to lay the foundation for the description of the invention—which relates to just one feature included within the pacemaker 10—that will follow.

Referring then to FIG. 1, it is seen that the dual-chamber pacemaker 10 is coupled to a heart 28 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 10 through a connector 73 that forms an integral part of the housing wherein the circuits of the pacemaker are housed.

The connector 73 is electrically connected to a protection network 77, which network 77 electrically protects the circuits within the pacemaker 10 from excessive shocks or voltages that could appear on the electrodes 75 and/or 77 in the event such electrodes were to come in contact with a high voltage signal, e.g., from a defibrillator shock.

The leads 74 and 76 carry stimulating pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (P-AMP) 82; and electrical signals from the ventricles are carried from the electrode 77, through the lead 76, to the input terminal of a ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture". (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.)

The dual-chamber pacemaker 10 is controlled by a control system 86 that typically includes a microprocessor programmed to carry out control and timing functions. The control system 86 receives the output signals from the atrial (P-AMP) amplifier 82 over signal line 88. Similarly, the control system 86 receives the output signals from the ventricular (R-AMP) amplifier 84 over signal line 90, and the output signals from the IEGM amplifier 85 over signal line 91. These output signals are generated each time that a P-wave, an R-wave, or an evoked response is sensed within the heart 28. The control system 86 also generates trigger signals that are sent to the atrial pulse generator (A-PG) 78 and the ventricular pulse generator (V-PG) 80 over signal lines 92 and 94, respectively. These trigger signals are generated each time that a stimulation pulse is to be generated by the respective pulse generator 78 or 80. The atrial trigger signal is referred to simply as the "A-trigger", and the ventricular trigger signal is referred to as the "V-trigger". During the time that either an A-pulse or V-pulse is being delivered to the heart, the corresponding amplifier, P-AMP 82 and/or R-AMP 84, is typically disabled by way of a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 1, the pacer 10 also includes a memory circuit 100 coupled to the control system 86 over a suitable data/address bus 102. This memory circuit 100 allows certain control parameters, used by the control system 86 in controlling the operation of the pacemaker, to be programmably stored and modified, as required, in order to customize the pacer's operation to suit the needs of a particular patient. Further, data sensed during the operation of the pacer may be stored in the memory 100 for later retrieval and analysis.

The memory 100 of the pacemaker 10 may take many forms, and may be subdivided into as many different memory blocks or sections (addresses) as needed in order to allow desired data and control information to be stored. A feature of the present invention is the ability to store a relatively large amount of sensed data as a data record, which data record may then be used to guide the operation of the device, e.g., whether RRT should be triggered. For example, the average battery voltage may be computed and stored on a regular basis, e.g., up to 32 times a day, with the last 120 monthly average measurements also being stored. Such information is useful for calculating longevity predictions and for time-versus-measurement graphs (generated by the external programmer). Other parameters, of course, in addition to (or in lieu of) battery voltage, may be similarly sensed, stored, averaged (or otherwise processed), and then used for comparison purposes, such as battery current, battery impedance, etc. Advantageously, modern memory devices allow for the storage of large amounts of data in this manner.

A clock circuit 103 directs an appropriate clock signal(s) to the control system 86, as well as to any other needed circuits throughout the pacemaker 10 (e.g., to the memory 100) by way of clock bus 105.

A telemetry/communications circuit 104 is further included in the pacer 10. This telemetry circuit 104 is connected to the control system 86 by way of a suitable command/data bus 106. In turn, the telemetry circuit 104, which is included within the implantable pacer 10, may be selectively coupled to an external programming device 108 by means of an appropriate communication link 110, which communication link 110 may be any suitable electromagnetic link, such as an RF (radio frequency) channel, a magnetic link, an inductive link, an optical link, and the like. Advantageously, through the external programmer 108 and the communication link 110, desired commands may be sent to the control system 86. Similarly, through this communication link 110 and the programmer 108, data (either held within the control system 86, as in a data latch, or stored within the memory 100) may be remotely received from the pacer 10. In this manner, non-invasive communications can be established with the implanted pacer 10 from a remote, non-implanted, location.

The pacer 10 additionally includes a battery 93 which provides operating power to all of the circuits of the pacer 70 via a POWER signal line 95. The voltage of the pacemaker battery 93 on the POWER signal line 95 is monitored by appropriate monitoring circuits within the control system 86, or elsewhere within the pacemaker 10, in order to ascertain whether the battery voltage has dropped below a predefined recommended replacement time (RRT) threshold. If so, as explained more fully below, then an RRT mode is invoked wherein the basic pacing interval of the pacemaker is increased (i.e., the basic pacing rate is slowed down). The manner in which this RRT mode is triggered is the subject of the present invention.

It is noted that the pacer 10 in FIG. 1 is referred to as a dual-chamber pacemaker because it interfaces with both the atria and the ventricles of the heart. Those portions of the pacer 10 that interface with the atria, e.g., the lead 74, the P-wave sense amplifier 82, the A-PG 78, and corresponding portions of the control system 86, are commonly referred to as the "atrial channel". Similarly, those portions of the pacer 10 that interface with the ventricles, e.g., the lead 76, the R-wave sense amplifier 84, the V-pulse generator 80, and corresponding portions of the control system 86, are commonly referred to as the "ventricular channel".

As needed for rate-responsive applications, the pacemaker 10 further includes at least one sensor 112 that is connected to the control system 86 of the pacer 10 over a suitable connection line 114. While this sensor 112 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, ph of blood, body motion, and the like. The type of sensor used is not critical to the present invention. Any sensor capable of sensing a parameter relatable to the rate at which the heart should be beating can be used. Such sensors are used with "rate-responsive" pacemakers in order to adjust the basic rate (pacing cycle) of the pacer in a manner that tracks the physiological needs of the patient. To this end, the control system 86 (when operating in a rate-responsive mode) receives output signals from the sensor 112 and converts them to a sensor-indicated-rate (SIR) signal which is used by the control system 86 to set the pacing interval of the pacemaker.

The pacemaker 10 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 10, and/or to signal the control system 86 that an external programmer 108 is in place to receive data from, or send data to, the pacemaker memory 100 or control system 86 through the telemetry communications circuits 104.

The telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art.

The control system 86 may be realized using a variety of different techniques and/or circuits. The preferred type of control system 86 is a microprocessor-based control system, as described below in conjunction with FIGS. 5–8. It is noted, however, that the control system 86 could also be realized using a state machine. Indeed, any type of control circuit or system could be employed for the control system 86. The present invention is not concerned with the details of the control system 26. Rather, it is concerned with the end result achieved by the control system, particularly relative to how the control system 86 triggers or generates an RRT signal or flag. Those of skill in the implantable medical device art, given the teachings presented herein, should thus be able to fashion numerous different types of control systems or circuits that achieve the desired device control and RRT trigger.

Representative of the types of control systems that could be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are all incorporated herein by reference.

The pacemaker 10 of FIG. 1 is a multi-mode programmable pacemaker. This means that, in addition to the parameters such as rate, pulse energy, and sensing thresholds, the basic operating mode of the pacemaker may be modified (via telemetry programming). The operating mode can also change as a result of an Auto Mode Switch. The operating modes (designated by conventional three letter codes as is known in the art) that may be programmed into the pacemaker 10 include: VOO, VVI, VVT, AOO, AAI, AAT, VDD, DOO, DVI, DDI, DDD, DDT, and VDI. Many of these pacemaker modes may also be operated in a rate-responsive mode, and when so programmed the designation of the operating mode may have a letter "R" added thereto, e.g., DDDR, VDDR, etc.

The "base rates" of the pacemaker 10 controls the pacing rate when the rate-responsive functions are not indicated. For AOO, AAI and AAT modes, the base rate interval is the interval from an atrial stimulus (A-pulse) to the next A-pulse without an intervening sensed event. For VOO, VVI, VDI, VVT, VDD, DOO, DVI, DDI and DDT modes, the base rate interval is the interval from a ventricular stimulus (V-pulse) to the next V-pulse without an intervening sensed event. In the DDD mode, the base rate interval in the interval from the A-pulse to the next expected A-pulse. If a sensed ventricular intrinsic event (R-wave) occurs in the AV interval, the pacer rate timing is not reset. When the battery depletes, and the pacer reaches the RRT condition, the pacing rate interval is increased by a prescribed amount, e.g., 100 milliseconds (ms). In a rate-responsive mode, the base rate is a function of the SIR.

During normal operation, when a magnet is not applied (i.e., when no magnet is sensed by the magnet detection circuit 87), then the criterion for RRT is defined as the time when the pacer's average cell impedance has increased to the point that, under its present load, cell terminal voltage has dropped to the lowest voltage necessary to maintain adequate pacer operation for a minimum of 3 months (6 months nominal before the predicted End of Life (EOL) of the pacemaker. Pacemaker EOL, in turn, is defined as the time when the output pulse (stimulus) amplitude drops to 50% of the programmed value. When EOL is reached, the pacemaker automatically reverts to a low-power consuming hardware backup circuit which implements a backup operating mode, such as VVI.

In accordance with one embodiment of the invention, the pacemaker's internal RRT detection circuit must detect a sustained battery voltage less than the programmed RRT trip point, or threshold voltage, before the RRT criterion is fulfilled. A sustained battery voltage is accomplished by monitoring and determining the average measured battery voltage. The average measured battery voltage is determined several times a day, e.g., 32 times a day. From such averages, a daily average is determined, as well as a monthly average. The last 120 monthly battery voltage average measurements may be stored in the pacemaker memory 100 (FIG. 1). Besides monitoring the battery voltage, the following additional analog parameters may also be monitored and stored in a similar manner: battery current, maximum battery current, battery impedance, atrial lead impedance, atrial pulse voltage, ventricular lead impedance, and ventricular pulse voltage.

A second battery voltage trip point, or second threshold voltage, programmed lower than the first RRT trip point, may also be used in some embodiments of the invention in order to immediately trigger the RRT condition (regardless of prior averages). Such second RRT voltage trip point thus protects against excessively low battery voltages.

When the RRT criterion is met, the base rate interval is increased by a prescribed amount, e.g., 100 ms. This increase in pacing interval causes a reduction in current being drawn from the pacemaker's battery and a corresponding increase in average battery voltage, thus permitting the pulse output voltage to be maintained. In accordance with this embodiment of the invention, this is the primary indicator of RRT. This increase in pacing interval brings about a corresponding decrease in pacing rate. Representative pacing rates at RRT for all programmable base rates are listed in Table 1 in units of PPM (pulses per minute).

TABLE I

RRT Rates

| PROGRAMMED RATE (PPM) | PACING RATE AT RRT (PPM) |
|---|---|
| 45 | 41.9 |
| 50 | 46.2 |
| 55 | 50.4 |
| 60 | 54.5 |
| 65 | 58.6 |
| 70 | 62.7 |
| 75 | 66.7 |
| 80 | 70.6 |
| 85 | 74.4 |
| 90 | 78.3 |
| 95 | 82.0 |
| 100 | 85.7 |
| 105 | 89.4 |
| 110 | 93.0 |
| 115 | 96.5 |
| 120 | 100.0 |
| 125 | 103.4 |
| 130 | 106.8 |
| 135 | 110.2 |
| 140 | 113.5 |
| 145 | 116.8 |
| 150 | 120.0 |
| 155 | 123.2 |
| 160 | 126.3 |
| 165 | 129.4 |
| 170 | 132.5 |

When RRT is indicated, the sensor 112 (FIG. 1) is automatically programmed to the "OFF" state, disabling rate-responsive operation. There is no reduction in the Maximum Sensor Rate prior to RRT.

In order to reduce the likelihood of prematurely detecting RRT during rate-responsive pacing, the present invention provides two additional ways to determine RRT whenever rate-responsive pacing is being used.

Figure 2:
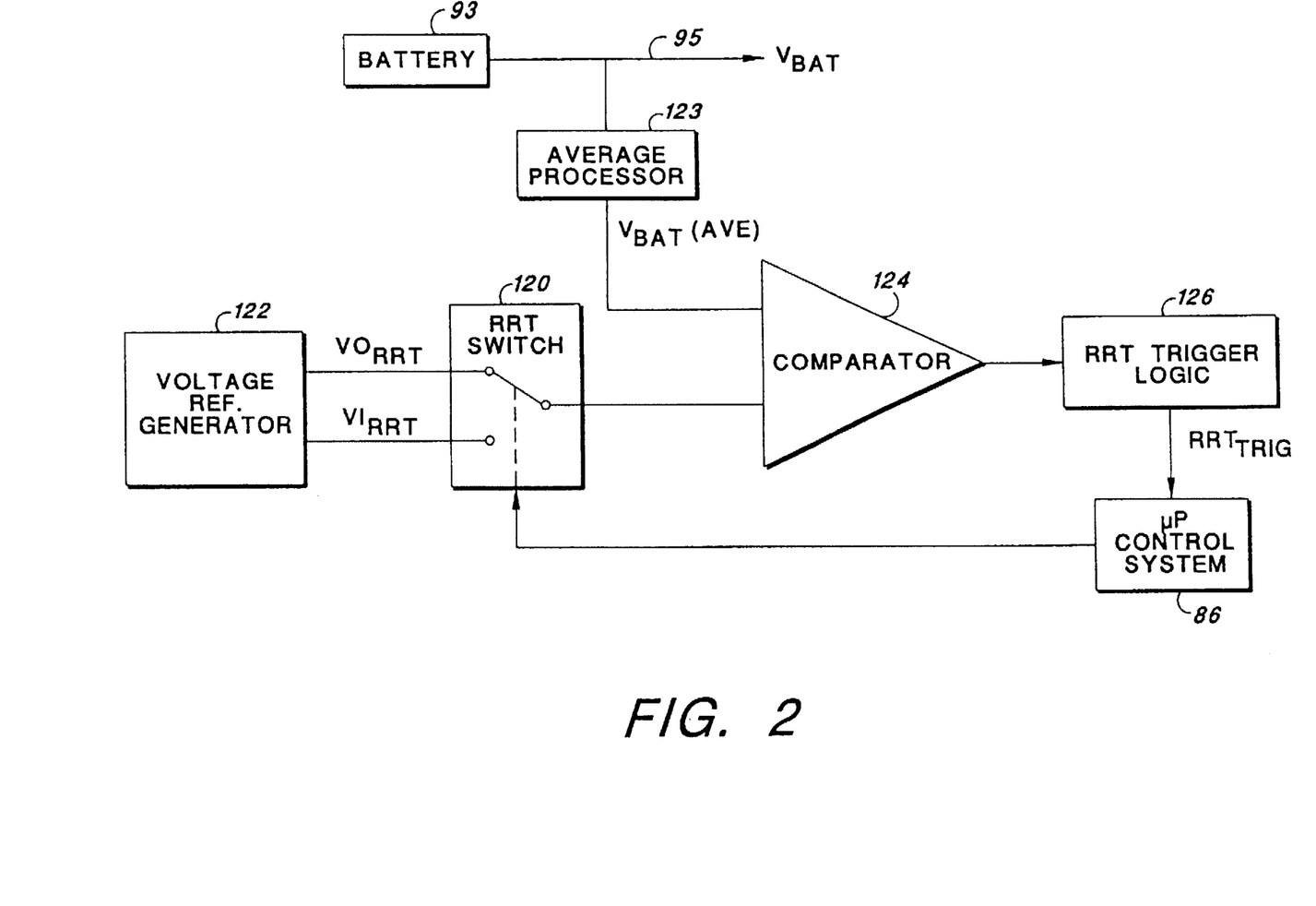
FIG. 2 is a functional block diagram of that portion of the pacemaker which implements the invention in accordance with an RRT logical switch embodiment of the invention.

The first rate-responsive-RRT-determining approach is illustrated by the functional block diagram shown in FIG. 2. Such approach uses a logical switch 120 to select one of a plurality of RRT threshold voltages against which the battery voltage is compared. It should be noted that FIG. 2 is a functional block diagram, used to illustrate the function carried out by this particular approach. In practice, the functions carried out in the block diagram of FIG. 2 can, for the most part, be carried out within the microprocessor-based control system 86, without the need for additional hardware circuits.

As seen in FIG. 2, the battery voltage $V_{BAT}$ available at the output terminals of the battery 93, i.e., as measured on the power bus 95, is averaged in a suitable average processor 123 in order to determine an average battery voltage $V_{BAT}$ (ave). Such average battery voltage is then compared, using comparator circuit 124, to a selected RRT threshold voltage. The RRT threshold voltage is selected by an RRT switch 120. At least two RRT threshold voltages, $V0_{RTT}$ and $V1_{RTT}$, each generated by an appropriate voltage reference generator circuit 122, may be selected by the switch 120 for application to the comparator circuit 124.

The comparator circuit 124 may be realized using an operational amplifier circuit as is known in the art if analog voltages are being compared. Alternatively, if the average battery voltage is converted to a digital signal, and if the RRT threshold voltages are likewise digital signals, then the comparison function performed by the comparator 124 can easily be performed by software/firmware within the microprocessor-based control system 86.

The selection of either $V0_{RRT}$ or $V1_{RRT}$ as the RRT threshold voltage is controlled by the control system 86 as a function of whether or not a rate-responsive pacing mode is being used by the pacemaker. If no rate-responsive pacing mode is employed, then the standard RRT threshold $V0_{RRT}$ is selected. If a rate-responsive pacing mode is employed, then the rate-responsive RRT threshold $V1_{RRT}$ is employed. The rate-responsive RRT threshold $V1_{RRT}$ is always set lower than the standard RRT threshold $V0_{RRT}$. Typically, $V1_{RRT}$ will be on the order of 200 mv less than $V0_{RRT}$.

Still referring to FIG. 2, it is seen that the output of the comparator circuit 124 is directed to appropriate RRT trigger logic circuit 126. In function, RRT trigger logic circuit 126 converts the output signal from the comparator circuit 124 to a suitable trigger signal, $RRT_{TRIG}$, which signals the control system 86 that RRT is indicated. If analog signals and circuits are used, the RRT trigger logic circuit 126 may be as simple as a one-shot multivibrator (pulse-generator) circuit. If digital signals are used, then the RRT trigger logic circuit 126 may be readily implemented in the software/firmware program code of the microprocessor-based control system 86.

Figure 3:
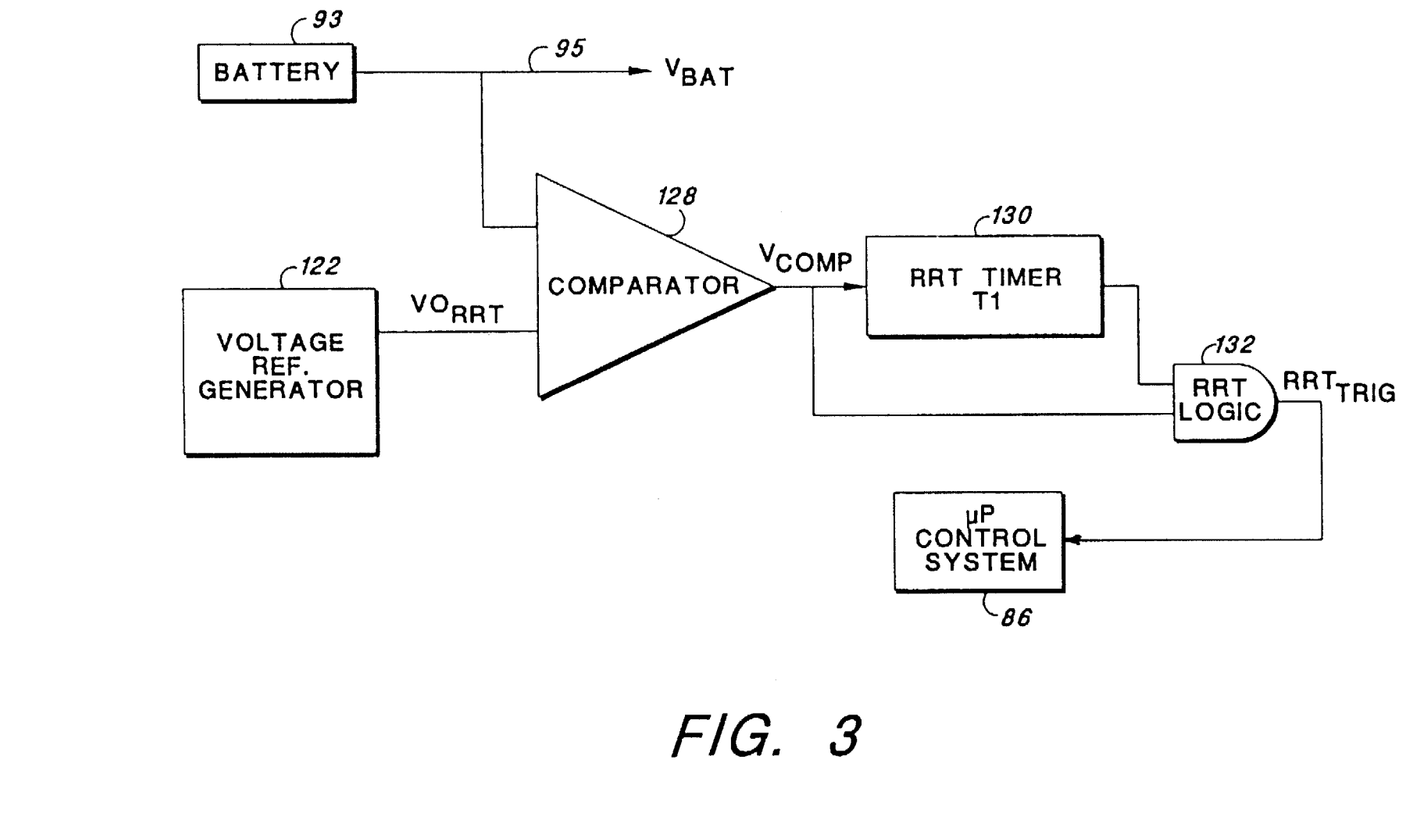
FIG. 3 is a functional block diagram of that portion of the pacemaker which implements the invention in accordance with an RRT-time-delay embodiment of the invention.

Turning next to FIG. 3, a functional block diagram of a second rate-responsive-RRT-determining approach is illustrated. Such approach uses an RRT delay timer 130 in order to delay issuance of the RRT trigger signal, $RRT_{TRIG}$, until a prescribed delay time period T1 has elapsed. Such prescribed time period T1 is preferably sufficiently long to be longer than a typical exercise duration (e.g. 4 hours). (In practice, it is noted that a similar effect is achieved by requiring that a sustained average of the battery average, $V_{BAT}(ave)$, be below a prescribed RRT threshold before triggering an RRT condition; particularly when "sustained" requires looking at the average battery voltage over a long time period, e.g., over a day or longer.)

As seen in FIG. 3, the battery voltage $V_{BAT}$ is compared with the RRT threshold voltage $V0_{RRT}$ in a suitable comparator circuit 128. As soon as the monitored battery voltage $V_{BAT}$ is less than the threshold voltage $V0_{RRT}$, then the RRT Timer 130 is triggered. Once triggered, the RRT Timer 130 must time out, unless reset (in which case it starts timing out all over again). If when the RRT timer times out the comparator circuit 128 indicates that $V_{BAT}$ has continuously remained less than $V0_{RRT}$ throughout the duration of the time delay set by the RRT Timer 130, then (and only then) is the RRT trigger signal, $RRT_{TRIG}$, generated by the RRT logic circuitry 132.

Figure 4:
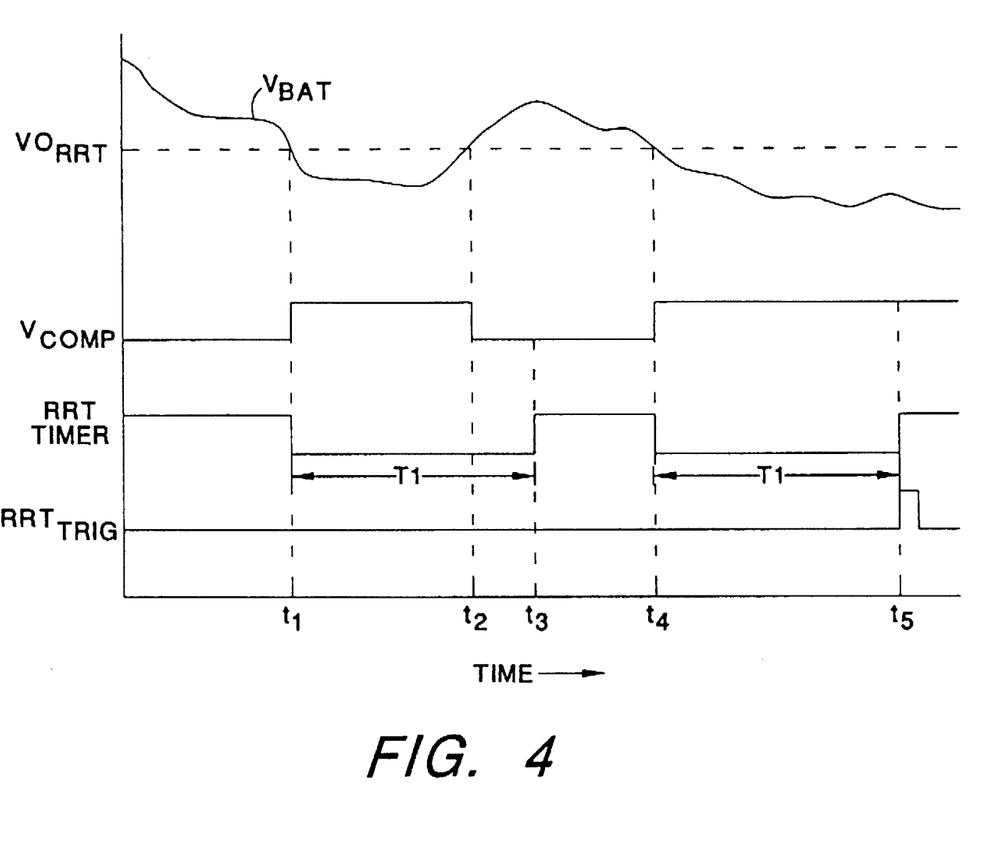
FIG. 4 is a timing diagram associated with the operation of the embodiment of FIG. 3.

The operation of the circuitry of FIG. 3 is illustrated in the timing waveform diagram of FIG. 4. As seen in FIG. 4, the battery voltage $V_{BAT}$ decreases over time as the battery cells become depleted and the internal impedance increases. As long as $V_{BAT}$ remains higher than the RRT threshold voltage $V0_{RRT}$, then the output signal, $V_{COMP}$, of the comparator circuit 128 remains low. At some point in time, e.g., at time t1, the battery voltage $V_{BAT}$ drops below the threshold voltage $V0_{RRT}$, causing $V_{COMP}$ to go high. This action (i.e., a low-to-high edge in the signal $V_{COMP}$) triggers the RRT timer circuit 130. Once triggered, the output signal of the timer circuit 130 goes low and remains low for a period of time T1. Any additional low-to-high edges in the input signal $V_{COMP}$ retrigger the start of the time delay T1. Thus, if the battery voltage $V_{BAT}$ oscillates about the threshold voltage $V0_{RRT}$, the RRT timer is retriggered, and the time period T1 restarts from the most recent occurrence of the $V_{COMP}$ signal triggering the RRT timer. Rapid changes in the battery voltage $V_{BAT}$, of course, may be minimized or eliminated by averaging the battery voltage over an appropriate time period before comparing it to the threshold voltage $V0_{RRT}$.

Still referring to FIG. 4, it is seen that at time t2, before the time period T1 has timed out, the battery voltage $V_{BAT}$ becomes greater than the RRT threshold voltage $V0_{RRT}$, causing the signal $V_{COMP}$ to go low. Thus, when T1 times out, at time t3, the signal $V_{COMP}$ is low. This means that the RRT logic circuitry 132 does not generate the $RRT_{TRIG}$ signal. In contrast, at time t4, $V_{BAT}$ again falls below the RRT threshold $V0_{RRT}$, causing $V_{COMP}$ to again go high, and triggering the time period T1. This time $V_{BAT}$ continuously remains below the RRT threshold $V0_{RRT}$ throughout the duration of T1, which ends at time t5. At time t5, because the battery voltage has continuously remained below the threshold voltage throughout the entire delay time T1, $V_{COMP}$ remains high at the timing out of T1. Thus, the RRT trigger signal, $RRT_{TRIG}$, is generated.

Figure 5:
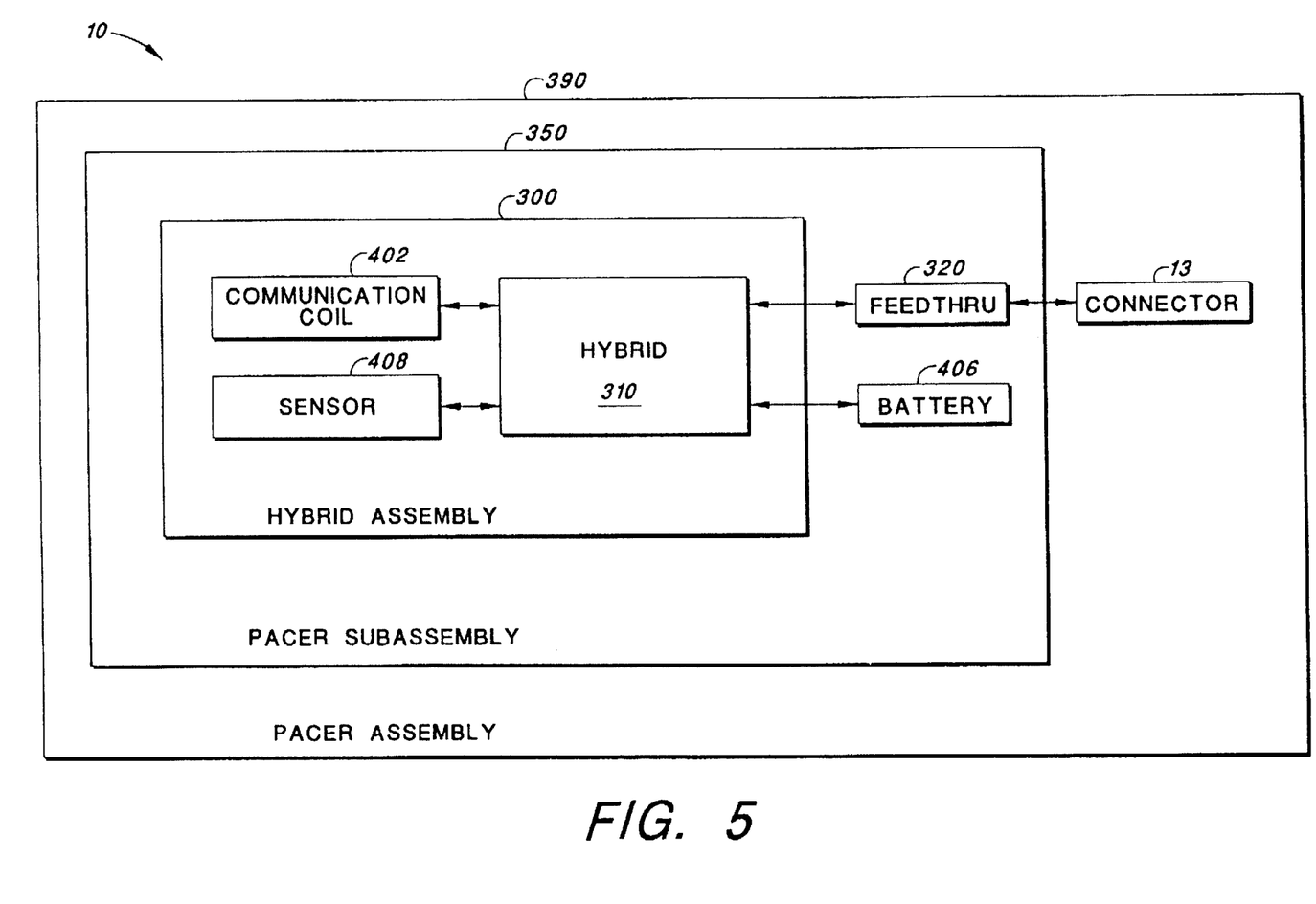
FIG. 5 is an assembly block diagram that depicts the various electrical/electronic hardware assemblies and subassemblies of an implantable pacemaker made in accordance with a microprocessor-based embodiment of the invention.

The above-described invention may be carried out using any type of implantable pacemaker which can be programmed, or operated, in the manner described. One type of pacemaker that may be used with the present invention is a multi-mode rate-responsive microprocessor-based pacemaker of the kind depicted in FIGS. 5–8. FIG. 5 depicts a block diagram of the various hardware assemblies and subassemblies that may be used within such a rate-responsive microprocessor-based pacemaker. As seen in FIG. 5, a pacemaker 10 is made up of a hybrid assembly 300, a pacer subassembly 350, and a pacer assembly 390. The hybrid assembly 300 includes almost all of the electronic circuitry and components of the pacemaker 10. Such circuitry and components include a communication coil 402, a sensor(s) 408 (which typically comprises a piezoelectric crystal used as an accelerometer), and a hybrid integrated circuit 310. The hybrid assembly 300 is combined with a battery 406 and feedthrough connectors 320 to form the pacer subassembly 350. All of the elements of the pacer subassembly 350 are housed in, or mounted to, a case 400 (FIG. 6) which is hermetically sealed. Electrical connection is made with the circuits sealed inside of the pacer subassembly 350 by way of the feedthrough connectors 320. Such feedthrough connectors 320 are then connected to the lead connector 13, attached to the pacer subassembly 350, in order to form the completed pacer assembly 390. The completed pacer assembly 390, when suitable pacing/sensing leads 74 and 76 (FIG. 1) are attached thereto through the connector 73, forms a functional pacemaker.

Figure 6:
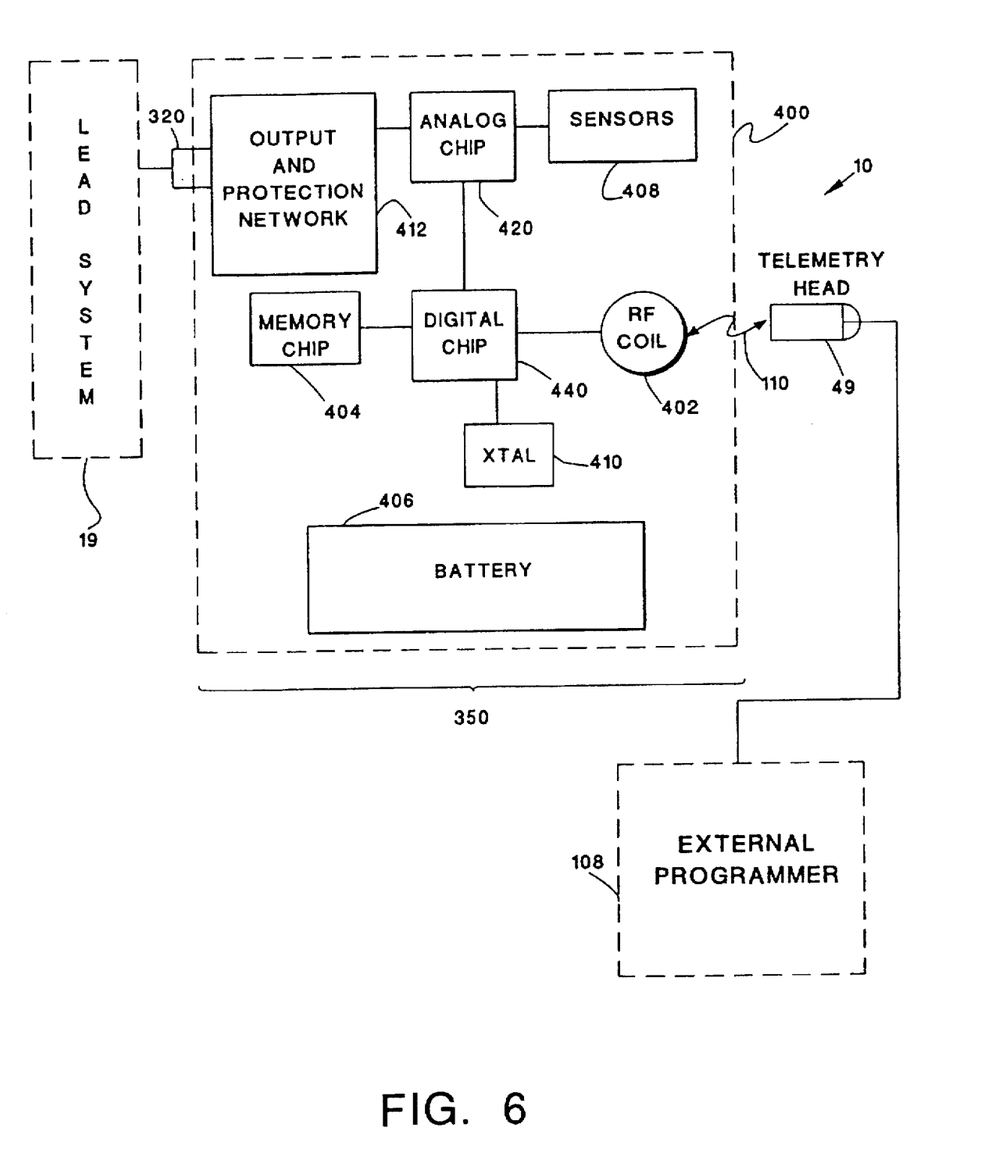
FIG. 6 is a block diagram of the hybrid assembly shown in FIG. 5.

Referring next to FIG. 6, a more detailed block diagram of the pacemaker 10, and particularly the pacer subassembly 350, is shown. As seen in FIG. 6, the pacemaker 10 and a lead system 19 (which lead system 19 comprises the leads 74 and 76, and the connector 73) are used with (i.e., programmed by and/or monitored with) the external programmer 108 (FIG. 1). The lead system 19 may also include an oxygen sensor lead, which lead contains a light emitting diode (LED) detector assembly used to measure the oxygen content of the blood. Such a lead is described, e.g., in U.S. Pat. No. 4,815,469, incorporated herein by reference.

The external programmer 108 includes a telemetry head 49 that is positioned proximate the implantable pacemaker 10 whenever a communication link 110 is to be established between the pacemaker 10 and the external programmer 108. The external programmer may be of conventional design, as described, e.g., in U.S. Pat. No. 4,809,697, incorporated herein by reference.

The components of the pacer subassembly 350 are housed within a suitable sealed case or housing 400 (which case or housing is represented in FIG. 6 by the dashed line 400). The case 400 is preferably a titanium metal case. The components within the case 400 include an RF coil 402, a memory chip 404, a battery 406, one or more physiological or other sensors in a sensor circuit 408, a crystal 410, an output/ protection network 412, an analog chip 420 and a digital chip 440.

The battery 406, which is by volume the largest component within the pacer subassembly 350, may be of conventional design, and is generally a lithium battery that provides operating power to all of the electronic circuits within the pacer subassembly. The RF coil 402 is used to establish the communication link 110 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 may be any suitable type of memory device wherein data may be stored and retrieved. Preferably the memory chip 404 is a low-power static random access memory (SRAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412 and the feedthrough connectors 320. The network 412 includes, e.g., output coupling capacitors and circuits which protect the analog chip 420 from high static or other voltages that might be coupled to the lead system 19, as are commonly used in implantable medical devices. The feedthrough connectors 320 allow electrical connection through the hermetically sealed case 400, and may be of conventional design.

Figure 7:
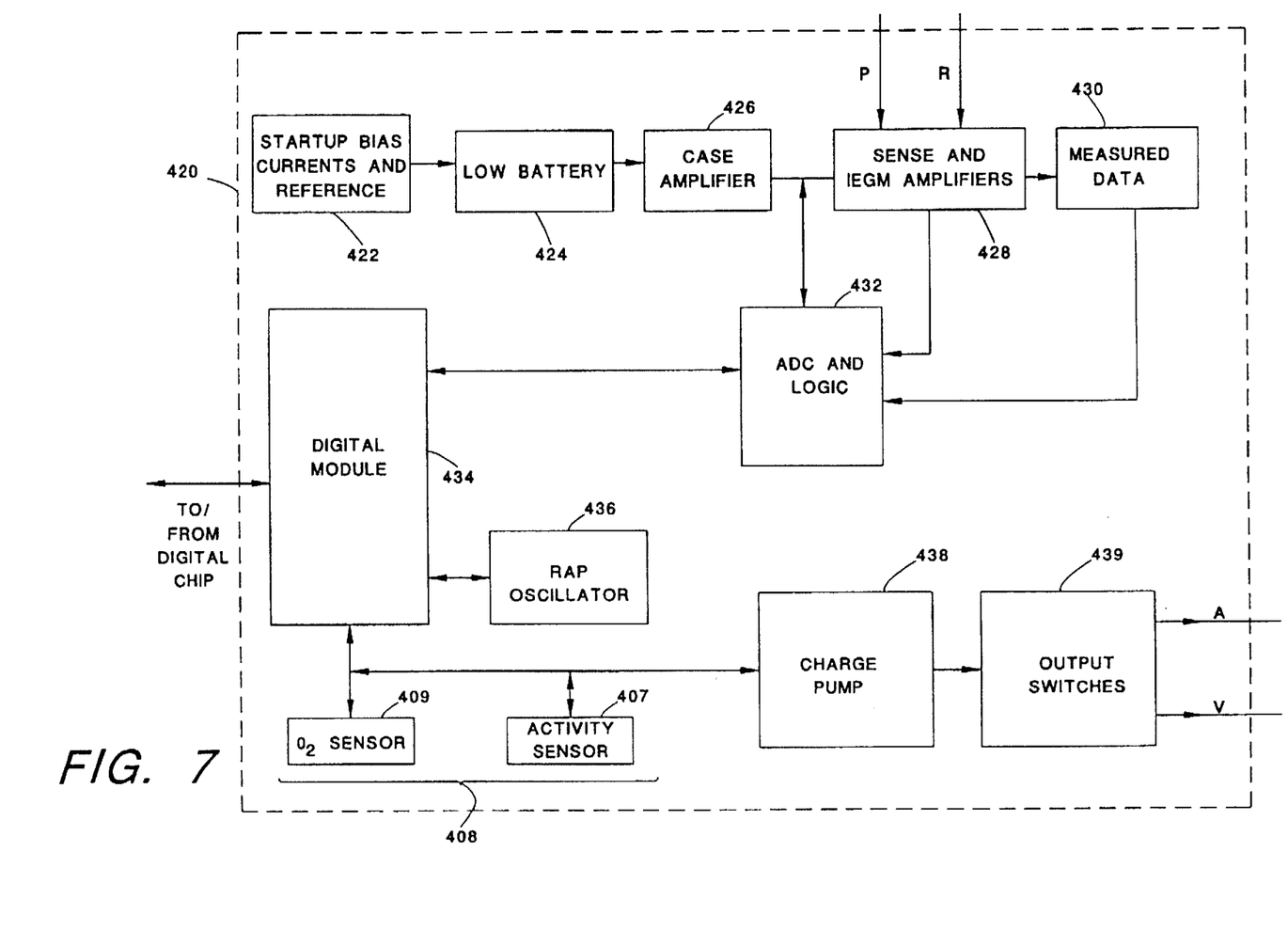
FIG. 7 is a block diagram of the analog chip portion of the hybrid assembly shown in FIG. 6.

Referring next to FIG. 7, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The sense and IEGM amplifier module 428 includes the P-wave amplifier 82 and the R-wave amplifier 84, described in FIG. 1. A measured data module 430 measures the battery voltage and current and other analog parameters of the pacing system. An ADC and Logic module 432 includes an analog-to-digital converter (ADC) and timing logic that are used to convert the analog signals of the pacemaker to 8-bit digital words. These digital words are then passed to a digital module 434, which module is used to generate all the basic timing and bus control functions as data is passed back and forth between the analog chip 420 and the digital chip 440.

Still referring to FIG. 7, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408 (also referred to as the sensor circuit 408). The sensor network 408 includes appropriate sensors for sensing activity and other parameters. For example, an 02 sensor circuit 409 may be used in conjunction with the oxygen sensor lead, when used, to measure blood oxygen of the patient. An activity sensor 407 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM WAVEFORMS, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 8:
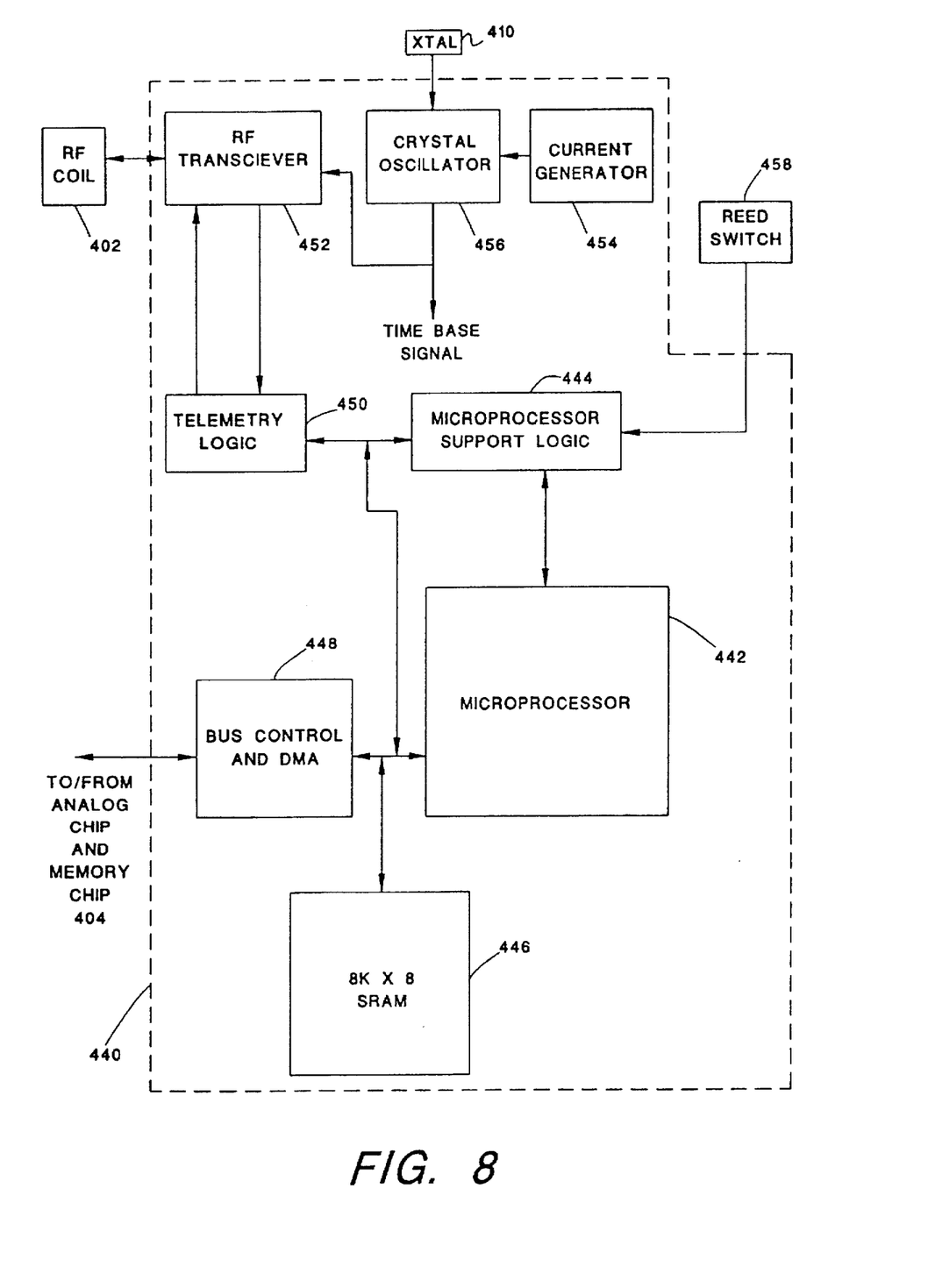
FIG. 8 is a block diagram of the digital chip portion of the hybrid assembly shown in FIG. 6, and illustrates the use of a microprocessor to control the operation of the pacemaker.

Turning next to FIG. 8, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit). In addition, an 8K by 8 static random access memory (SRAM) 446, or equivalent memory element, is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide direct memory access (DMA) timing and control of data transfer with the analog chip 420, and the memory chip 404, including timing and control of the analog-to-digital converter 432 (FIG. 13) and telemetry data. Telemetry logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 108 through the telemetry head 49 (see FIG. 6). A crystal oscillator circuit 456, in conjunction with the crystal 410 (external to the digital chip 440) provides a crystal-controlled time base signal for the pacemaker system. A current generator 454 provides the bias currents for the digital chip. A reed switch 458 (external to the digital chip 440) is coupled to the microprocessor support logic 444. The reed switch 458 detects the presence of a magnetic field, which magnetic field is present whenever the telemetry head 49 (FIG. 6) is in place on the patient's skin above the location where the pacemaker is implanted.

The pacemaker architecture and circuitry described in connection with FIGS. 5-8 provides the basic functions of the pacemaker described in connection with FIG. 1, plus other pacing/sensing functions as are known in the art. For purposes of the present invention, the pacemaker circuitry of FIGS. 5-8 monitors the battery voltage and/or current and determines an average thereof, applies the appropriate RRT threshold, determines whether the measured and RRT threshold has been reached, and if so, triggers the RRT in the manner described above in connection with FIGS. 2–4, or equivalent methods and/or techniques, thereby providing for an accurate RRT indicator which provides for the full rate response of the pacemaker until RRT is indicated without any decrease in longevity due to a premature tripping of RRT during a rate-responsive mode.

While the invention herein disclosed has been described by means of specific embodiments and applications thereof, numerous modifications and variations could be made thereto by those skilled in the art without departing from the scope of the invention set forth in the claims.

What is claimed is:

1. A method of generating a recommended replacement time (RRT) trigger signal for use in an implantable multi-mode pacemaker, at least one of the modes of said pacemaker comprising a rate-responsive mode, comprising:
    (a) regularly monitoring the battery voltage, $V_{BAT}$, of said multi-mode pacemaker;
    (b) generating an RRT trigger signal whenever the monitored battery voltage drops below a first prescribed RRT threshold whenever a non-rate-responsive mode of the pacemaker is in use;
    (c) generating the RRT trigger signal whenever the monitored battery voltage drops below a second prescribed threshold whenever a rate-responsive mode of the pacemaker is in use, where the second prescribed RRT threshold is lower than the first prescribed RRT threshold; and
    (d) increasing the pacemaker's basic pacing interval by a prescribed amount in response to generation of the RRT trigger signal.

2. The method of claim 1 wherein step (a) comprises monitoring the battery voltage at a prescribed sampling rate and determining an average battery voltage, $V_{BAT}(ave)$, based on the last n samples of the battery voltage.

3. A method of generating a recommended replacement time (RRT) trigger signal for use in an implantable multi-mode pacemaker comprising:
    (a) regularly measuring the battery voltage, $V_{BAT}$, of said multi-mode pacemaker;
    (b) determining a sustained battery voltage based on the previous measurements of the battery voltage over a prescribed time period;
    (c) generating an RRT trigger signal whenever the sustained battery voltage drops below a first prescribed RRT threshold; and
    (d) increasing the pacemaker's basic pacing interval by a prescribed amount in response to generation of the RRT trigger signal.

4. The method of claim 3 wherein step (d) includes increasing the basic pacing interval by 100 ms in response to generation of the RRT trigger signal.

5. The method of claim 3 wherein the step of determining a sustained battery voltage comprises determining an average battery voltage over a period of time longer than 4 hours.

6. The method of claim 3 wherein the step of regularly measuring the battery voltage comprises measuring the battery voltage at least 32 times a day.

7. A method of generating a recommended replacement time (RRT) trigger signal for use in an implantable multi-mode pacemaker, at least one of the modes of said pacemaker comprising a rate-responsive mode, comprising:
    (a) regularly measuring the battery voltage, $V_{BAT}$, of said multi-mode pacemaker;
    (b) immediately generating an RRT trigger signal whenever the measured battery voltage drops below a first prescribed RRT threshold whenever a non-rate-responsive mode of the pacemaker is in use;
    (c) generating, whenever a rate-responsive mode of the pacemaker is in use; the RRT trigger signal only after a programmable delay T1 has elapsed during which the monitored battery voltage has continuously remained below the first prescribed RRT threshold throughout the delay T1; and
    (d) increasing the pacemaker's basic pacing interval by a prescribed amount in response to generation of the RRT trigger signal.

8. The method of claim 7 wherein step (c) includes generating the RRT trigger signal, when a rate-responsive mode of the pacemaker is in use, only when the battery voltage drops below and continuously remains below the first prescribed threshold for a delay T1 that is longer than a typical exercise duration.

9. The method of claim 8 further including defining the delay T1 to be at least four hours.

10. The method of claim 7 comprising determining an average battery voltage, $V_{BAT}(ave)$, based on the measured battery voltage over a period of time that is at least one day; comparing the $V_{BAT}(ave)$ determination against the first prescribed RRT threshold; and generating the RRT trigger signal only when $V_{BAT}(ave)$ falls below the first prescribed RRT threshold.

11. A multi-mode rate-responsive pacemaker comprising:
    a battery;
    means coupled to the battery for generating pacing stimuli at a basic pacing interval;
    means for measuring the battery voltage on a regular basis;
    means for comparing the measured battery voltage to a selected one of a plurality of RRT threshold voltages;
    means for generating an RRT trigger signal whenever the measured battery voltage falls below the selected one of the plurality of RRT threshold voltages; and
    means for increasing the basic pacing interval of the pacemaker in response to generation of the RRT trigger signal.

12. The multi-mode rate-responsive pacemaker of claim 11 further including means for selecting a first one of the plurality of RRT threshold voltages whenever the pacemaker is operating in a non-rate-responsive mode, and means for selecting a second one of the plurality of RRT threshold voltages whenever the pacemaker is operating in a rate-responsive mode.

13. The multi-mode rate-responsive pacemaker of claim 12 wherein the second one of the plurality of RRT threshold voltages is less than the first one of the plurality of RRT threshold voltages.

14. The multi-mode rate-responsive pacemaker of claim 13 wherein the second one of the plurality of RRT threshold voltages is less than the first one of the plurality of RRT threshold voltages by at least 100 mv.

15. The multi-mode rate-responsive pacemaker of claim 12 wherein the means for measuring the battery voltage on a regular basis comprises means for determining an average battery voltage.

16. A multi-mode rate-responsive pacemaker comprising:

a battery;

means coupled to the battery for generating pacing stimuli at a basic pacing interval;

means for measuring an average battery voltage;

means for comparing the average battery voltage to a prescribed RRT threshold voltage;

means for immediately generating an RRT trigger signal whenever the average battery voltage falls below the prescribed RRT threshold voltage if the pacemaker is operating in a non-rate-responsive mode of operation;

means for generating an RRT trigger signal after a prescribed delay, when the pacemaker is operating in a rate-responsive mode of operation, and when the average battery voltage continuously remains below the prescribed RRT threshold voltage throughout the prescribed delay; and means for increasing the basic pacing interval of the pacemaker in response to generation of the RRT trigger signal.

17. The multi-mode rate-responsive pacemaker of claim 16 wherein the prescribed delay comprises a time delay longer than a typical exercise duration.

18. The multi-mode rate-responsive pacemaker of claim 17 wherein the prescribed delay comprises a time delay of at least four hours.

* * * * *